(12) United States Patent
Wu (10) Patent No.: US 11,090,820 B1
(45) Date of Patent: Aug. 17, 2021

(54) BLADE HOLDER FOR ASSEMBLING A REPLACEABLE BLADE

(71) Applicant: Chien-Hsin Wu, New Taipei (TW)

(72) Inventor: Chien-Hsin Wu, New Taipei (TW)

( * ) Notice: Subject to any disclaimer, the term of this patent is extended or adjusted under 35 U.S.C. 154(b) by 22 days.

(21) Appl. No.: 16/809,241

(22) Filed: Mar. 4, 2020

(51) Int. Cl.
  *B26B 5/00* (2006.01)
  *A61B 17/3213* (2006.01)

(52) U.S. Cl.
  CPC ............ *B26B 5/00* (2013.01); *A61B 17/3213* (2013.01)

(58) Field of Classification Search
  None
  See application file for complete search history.

(56) References Cited

U.S. PATENT DOCUMENTS

| | | | | |
|---|---|---|---|---|
| 2,708,313 | A * | 5/1955 | Steele | A61B 17/3213 30/339 |
| 4,617,738 | A * | 10/1986 | Kopacz | A61B 17/3213 30/339 |
| 4,922,614 | A * | 5/1990 | Machida | A61B 17/3213 30/339 |
| 5,475,925 | A * | 12/1995 | Newman | B26B 5/001 30/162 |
| 8,074,364 | B2 | 12/2011 | Nakamura | |
| 9,586,329 | B2 * | 3/2017 | Schuft | B26B 5/001 |
| 10,525,606 | B2 * | 1/2020 | Cheng | B26B 1/044 |
| 2017/0151682 | A1 | 6/2017 | Cheng | |
| 2019/0217489 | A1 | 7/2019 | Cheng | |

* cited by examiner

*Primary Examiner* — Hwei-Siu C Payer
(74) *Attorney, Agent, or Firm* — Muncy, Geissler, Olds & Lowe, P.C.

(57) ABSTRACT

A blade holder for assembling a replaceable blade comprises a supporting base assembling with a shank, a mounting rod integrally extending from the supporting base, and a blade limiting assembly. The mounting rod is formed with a first mounting hole. The blade limiting assembly comprises a limiting member provided on the mounting rod and is controlled to move a displacement stroke relative to the mounting rod, a limiting block provided in the first mounting hole, and an elastic member provided in the first mounting hole and connected to the limiting block. The limiting member comprises a limited position and an unblocked position in the displacement stroke. The limiting block is located on a path of the displacement stroke, and the limiting block comprises a stop position that the limiting block protrudes a surface of the mounting rod, and a release position that sinks into the first mounting hole.

14 Claims, 7 Drawing Sheets

BLADE HOLDER FOR ASSEMBLING A REPLACEABLE BLADE

FIELD OF THE INVENTION

The present invention relates to a blade holder for assembling a replaceable blade, and more particularly to a blade holder provided with a blade limiting assembly.

BACKGROUND OF THE INVENTION

In the present, manufacturers have introduced cutting tools capable of replacing blades, such as disclosed in U.S. Pat. No. 8,074,364 and US 2017/0151682A1. However, in the use of the aforementioned cutting tools, it is easy for users to accidentally detach a replaceable blade mounted on a blade holder to cause danger.

In order to solve the foregoing problem, US 2019/0217489 provides a cutting tool and a shank structure of the cutting tool. The cutting tool is capable of quickly and safely replacing and stably positioning a blade. As shown in the figure, the cutting tool is composed of a blade (equivalent to the replaceable blade described above), an engage and push plate, and an engaged position seat sequentially. A first connecting rod is fixed to the engaged push plate and is movably inserted in the blade and the engaged position seat. An engage block is fixed to the engaged position seat, and is movably inserted in the blade and the engaged push plate. When the blade, the engage and push plate as well as the engaged position seat are assembled integrally, the first connecting rod is locked on the engaged position seat. After a user presses a pushed unlock button, the first connecting rod is released from the current locked state to push the engaged push plate and the blade simultaneously. The user pushes the blade to cause the blade to be detached from the engage block, so that the user can easily remove and replace the blade in a safety manner. In fact, US 2019/0217489 can only restricts movement of the engaged push plate by the pushed unlock button, if the user accidentally presses the pushed unlock button during the use of the cutting tool, it may cause the replaceable blade to detach, and therefore a problem of safety still exist.

SUMMARY OF THE INVENTION

A main object of the present invention is to solve the problem caused the conventional structures being incapable of specifically limiting and preventing users from accidentally pressing to cause the replaceable blade to erroneously detach.

In order to achieve the above-mentioned object, the present invention provides a blade holder for assembling a replaceable blade. The replaceable blade comprises a long assembling hole, and the long assembling hole comprises a wide hole section and a narrow hole section that communicates with the wide hole section and is close to a blade point. The blade holder comprises a supporting base, a mounting rod and a blade limiting assembly. The supporting base is assembled with a shank and provided for a heel of the replaceable blade to dispose thereon. The mounting rod is integrally extended from the supporting base and capable of being placed in the wide hole section. The mounting rod comprises an assembling rail disposed at one end opposite to the supporting base and a first mounting hole, wherein the assembling rail is engaged with the narrow hole section when the replaceable blade is assembled in a direction toward the supporting base. The blade limiting assembly comprises a limiting member provided on the mounting rod and is controlled to move a displacement stroke relative to the mounting rod, a limiting block provided in the first mounting hole, and an elastic member provided in the first mounting hole and connected to the limiting block. The limiting member comprises a limited position and an unblocked position in the displacement stroke. The limiting block is located on a path of the displacement stroke, and the limiting block comprises a stop position that the limiting block protrudes a surface of the mounting rod to force the limiting member to locate at the limited position, and a release position that the limiting block is sunk into the first mounting hole to allow the limiting member to switch between the limited position and the unblocked position. The blade limiting assembly comprises a first mode that the limiting block enters the stop position to prohibit the heel from detaching from the blade holder by the limiting member when the replaceable blade is mounted on the blade holder, and a second mode that the limiting block enters the release position to allow the limiting member to switch position so that the replaceable blade is detached relative to the blade holder.

In one embodiment, a first protruded rib is provided in the first mounting hole to prevent the limiting block from detaching, and the limiting block comprises a main body and a second protruded rib disposed on one edge of the main body to abut against the first protruded rib when the limiting block enters the stop position.

In one embodiment, the mounting rod is provided with a mounting slot on one side where the limiting block protrudes, and the limiting member comprises a mounting portion placed in the mounting slot, and a push portion connected to the mounting portion and located on the surface of the mounting rod.

In one embodiment, the mounting slot is opened at one side facing the supporting base, and the supporting base comprises a groove disposed extendedly from the mounting slot for the mounting portion to slide in the groove.

In one embodiment, the limiting member comprises a long hole penetrating the mounting portion and the push portion, and the mounting rod comprises a second mounting hole opened in the mounting slot, and a positioning member passing through the long hole to be assembled in the second mounting hole.

In one embodiment, the first mounting hole and the second mounting hole penetrate the mounting rod, the blade limiting assembly comprises a supporting plate provided on one side of the mounting rod without the limiting block protruding from, and the supporting plate is provided for assembling the positioning member and the elastic member.

In one embodiment, the supporting plate comprises a fixed end assembled with the positioning member, and a free end assembled with the elastic member and displacing in a direction opposite to the mounting rod when the limiting block is in the release position.

In one embodiment, the supporting base comprises a hinge joint portion assembling with the shank.

Compared with the prior art, the invention provides the blade holder for assembling the replaceable blade which can solve the problem of the conventional structures that fail to specifically limit and prevent users from accidentally pressing to cause the replaceable blade to erroneously detach.

DETAILED DESCRIPTION OF THE PREFERRED EMBODIMENTS

The detailed description and technical contents of the present invention are described below with reference to the drawings.

Figure 1:
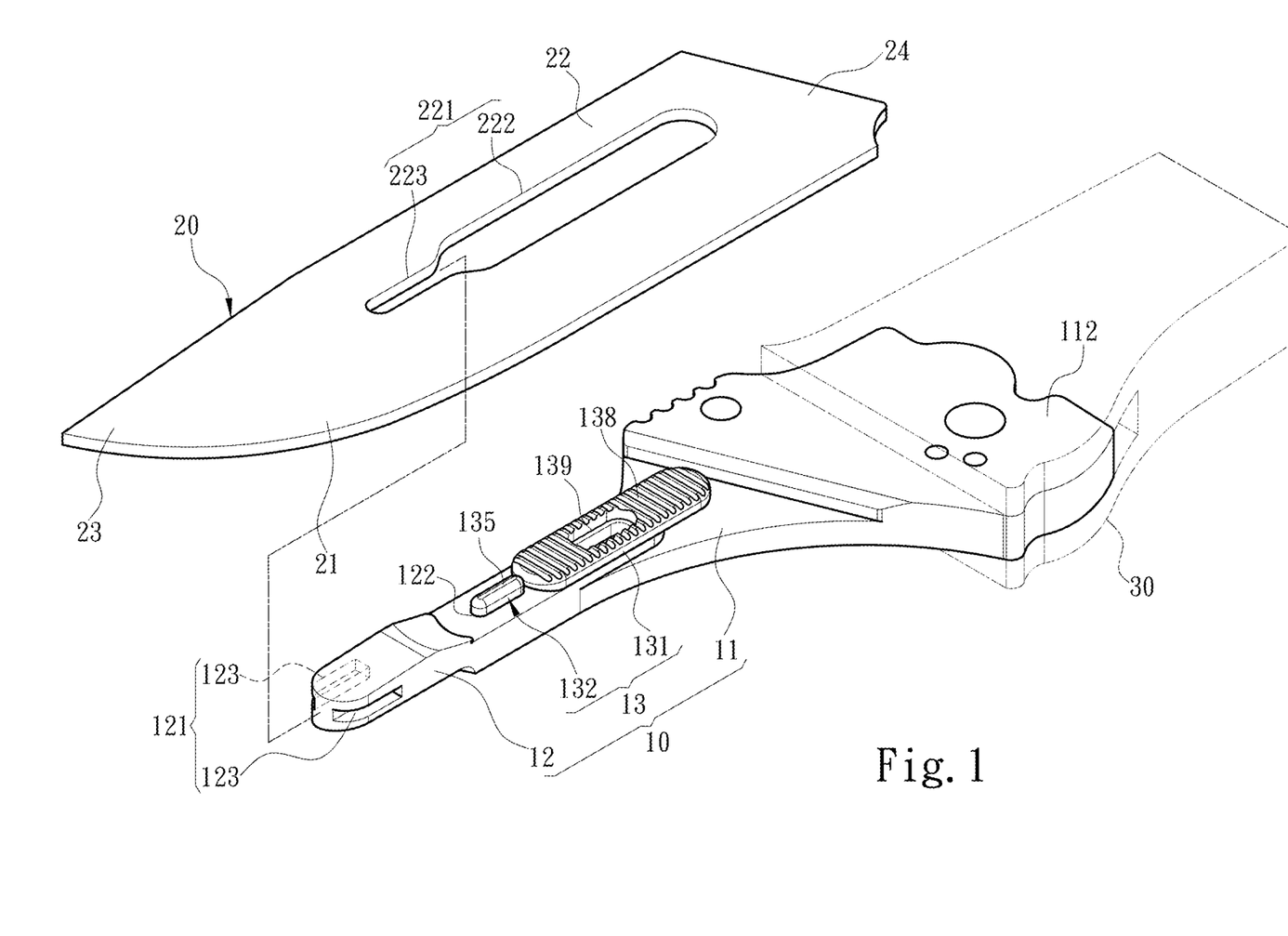
FIG. 1 is an exploded perspective view of a cutting tool according to an embodiment of the present invention.
Figure 2:
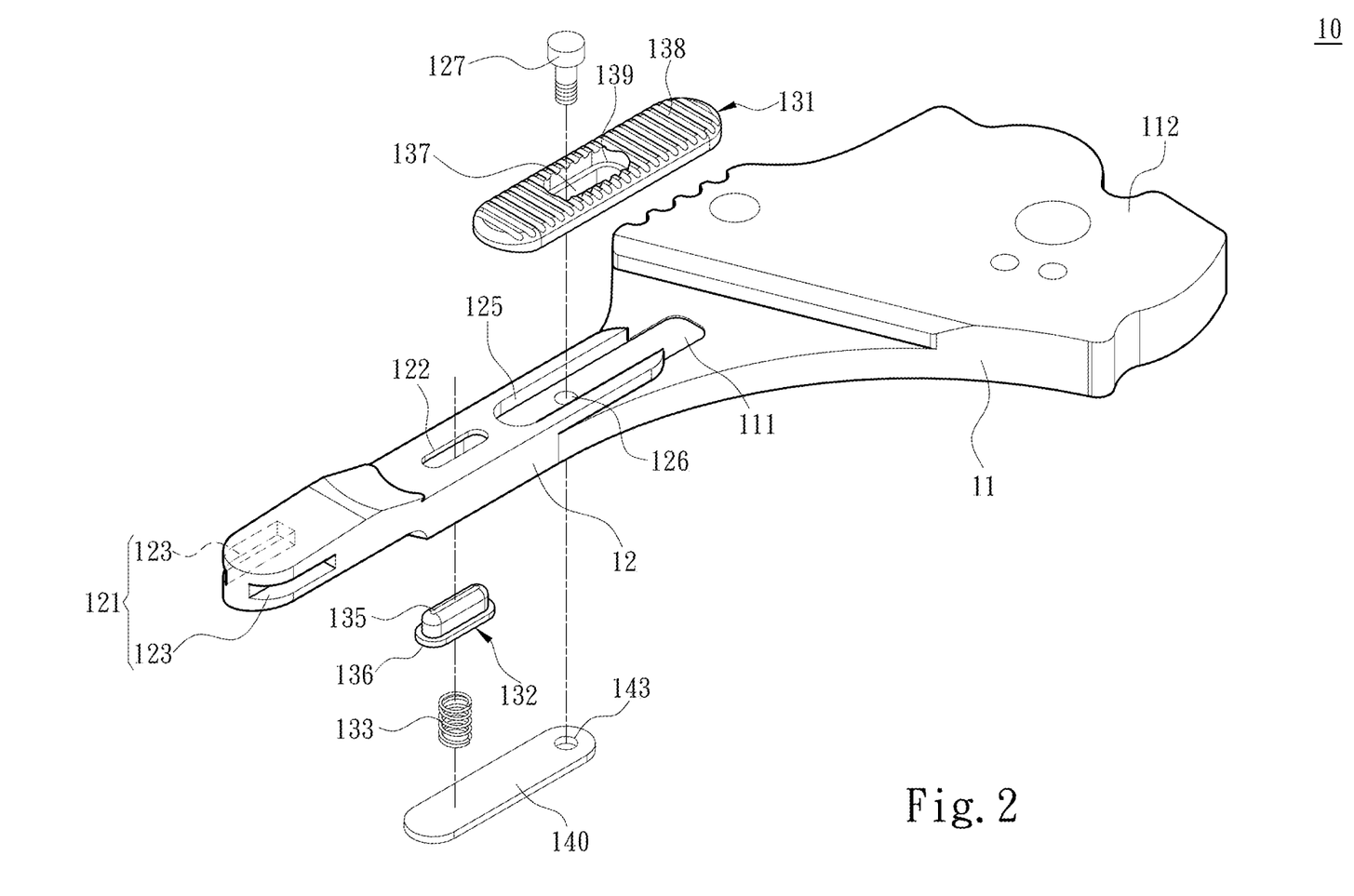
FIG. 2 is a first exploded perspective view of a blade holder according to an embodiment of the present invention.
Figure 3:
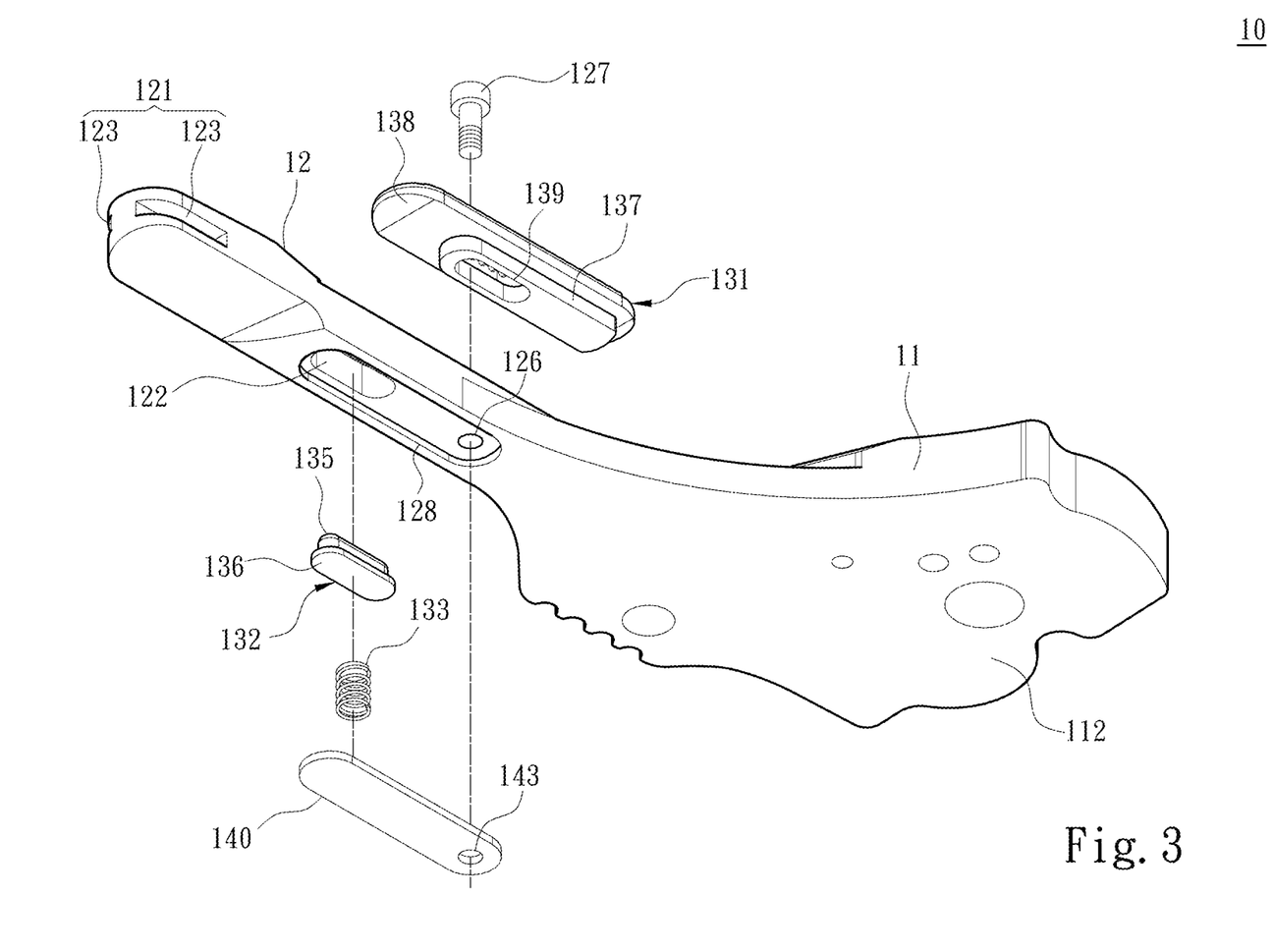
FIG. 3 is a second exploded perspective view of the blade holder according to an embodiment of the present invention.

Please refer to FIG. 1, FIG. 2, and FIG. 3. The present invention provides a blade holder 10, the blade holder 10 is combined with a replaceable blade 20 and a shank 30 to form a cutting tool. The replaceable blade 20 is not limited to be implemented as a single type of blade edge structure, and the cutting tool can be equipped with different functions according to the selected replaceable blade 20. Further, the replaceable blade 20 can be slightly bent when subjected to a force. The replaceable blade 20 is divided into a blade edge portion 21 and a body portion 22. The replaceable blade 20 comprises a long assembling hole 221 provided on the body portion 22, and the long assembling hole 221 penetrates two sides of the body portion 22. The long assembling hole 221 comprises a wide hole section 222 and a narrow hole section 223 that communicates with the wide hole section 222 and is close to a blade point 23. The blade holder 10 comprises a supporting base 11, a mounting rod 12, and a blade limiting assembly 13. The supporting base 11 is assembled with the shank 30 and is provided for a heel 24 of the replaceable blade 20 to dispose on the supporting base 11, wherein the heel 24 is a part of the body portion 22. In addition, the mounting rod 12 integrally extends from the supporting base 11, and a contour of the mounting rod 12 matches the wide hole section 222 of the long assembling hole 221, so that the mounting rod 12 is capable of being placed in the wide hole section 222. The mounting rod 12 comprises an assembling rail 121 disposed at one end opposite to the supporting base 11, and a first mounting hole 122. Further, the assembling rail 121 comprises two notches 123 located on the mounting rod 12. The assembling rail 121 is engaged with the narrow hole section 223 of the long assembling hole 221 when the replaceable blade 20 is assembled in a direction toward the supporting base 11, and a length of the assembling rail 121 is the same as a length of the narrow hole section 223.

Please refer to FIG. 2, FIG. 3, FIG. 4, and FIG. 5. The blade limiting assembly 13 includes a limiting member 131 provided on the mounting rod 12, a limiting block 132 provided in the first mounting hole 122, and an elastic member 133 provided in the first mounting hole 122 and connected to the limiting block 132. Further, the limiting member 131 is operated to generate a displacement stroke 134 relative to the mounting rod 12, that is, the limiting member 131 can be pushed by an external force to slide relative to the mounting rod 12. The limiting member 131 has a limited position and an unblocked position in the displacement stroke 134. The limiting member 131 enters either position according to a direction of force applying on the limiting member 131. Specifically, when the limiting member 131 is subjected to a force applying toward the supporting base 11, the limiting member 131 will enter the limited position. By contrast, when the limiting member 131 is subjected to a force applying toward a direction opposite to the supporting base 11, the limiting member 131 will enter the unblocked position. Furthermore, the first mounting hole 122 is partially covered when the limiting member 131 is in the unblocked position. On the other hand, the limiting block 132 is located on a path of the displacement stroke 134. The limiting block 132 has a stop position that the limiting block 132 is not pressed to protrude a surface of the mounting rod 12, and a release position that the limiting block 132 is pressed to sink into the first mounting hole 122. Further, when the limiting block 132 is located at the stop position, the limiting member 131 fails to be displaced toward a direction opposite to the supporting base 11, so that the limiting member 131 is limited to be located at the limited position. When the limiting block 132 is located at the release position, the limiting block 132 does not interfere with movement of the limiting member 131 and allows the limiting member 131 to switch between the limited position and the unblocked position. Furthermore, the limiting block 132 not only can be sunk into the first mounting hole 122 by applying an external force, but also can be pressed by the limiting member 131 which is moved to the unblocked position.

Figure 6:
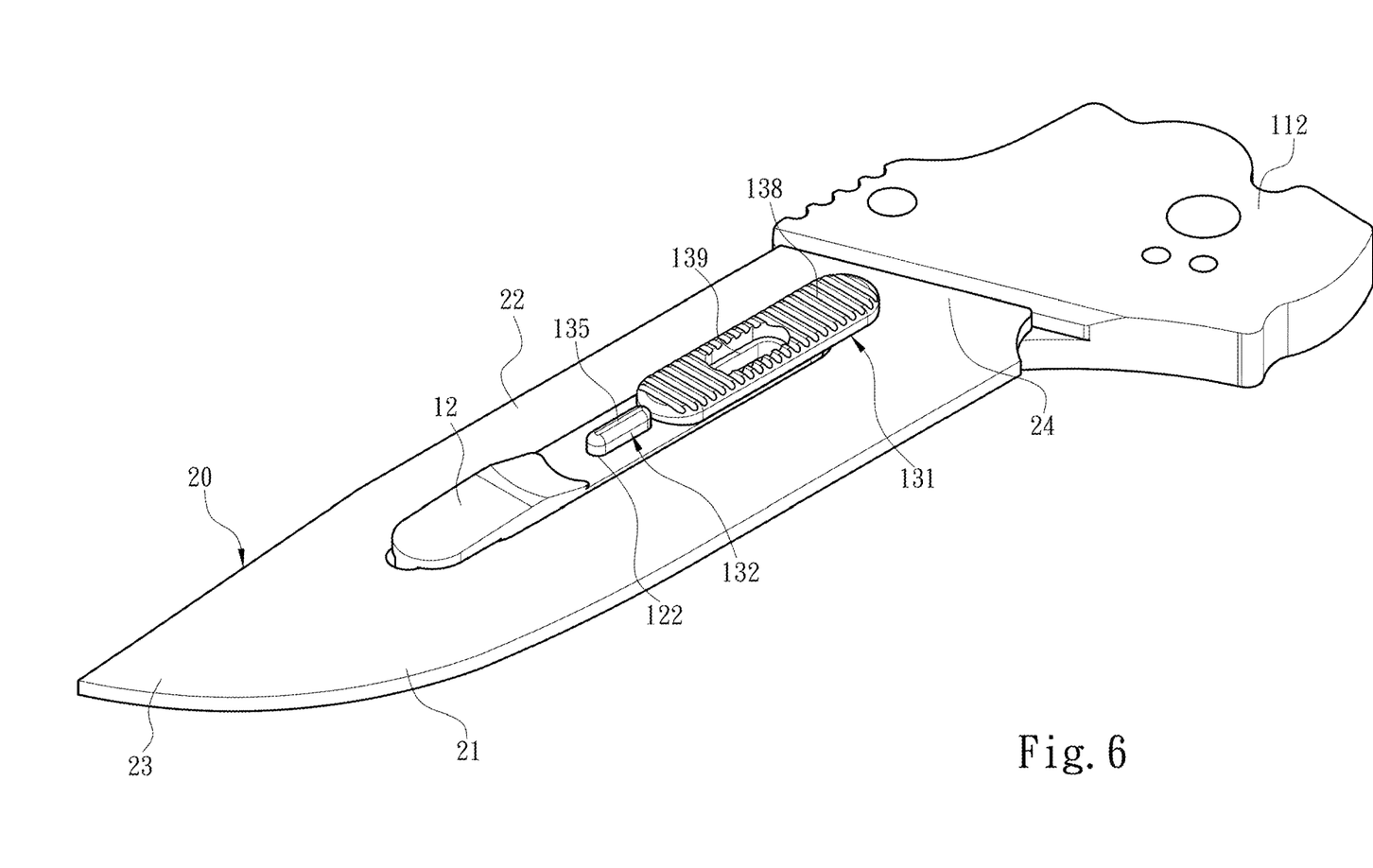
FIG. 6 is a perspective structural view of the cutting tool in a first mode according to an embodiment of the present invention.
Figure 7:
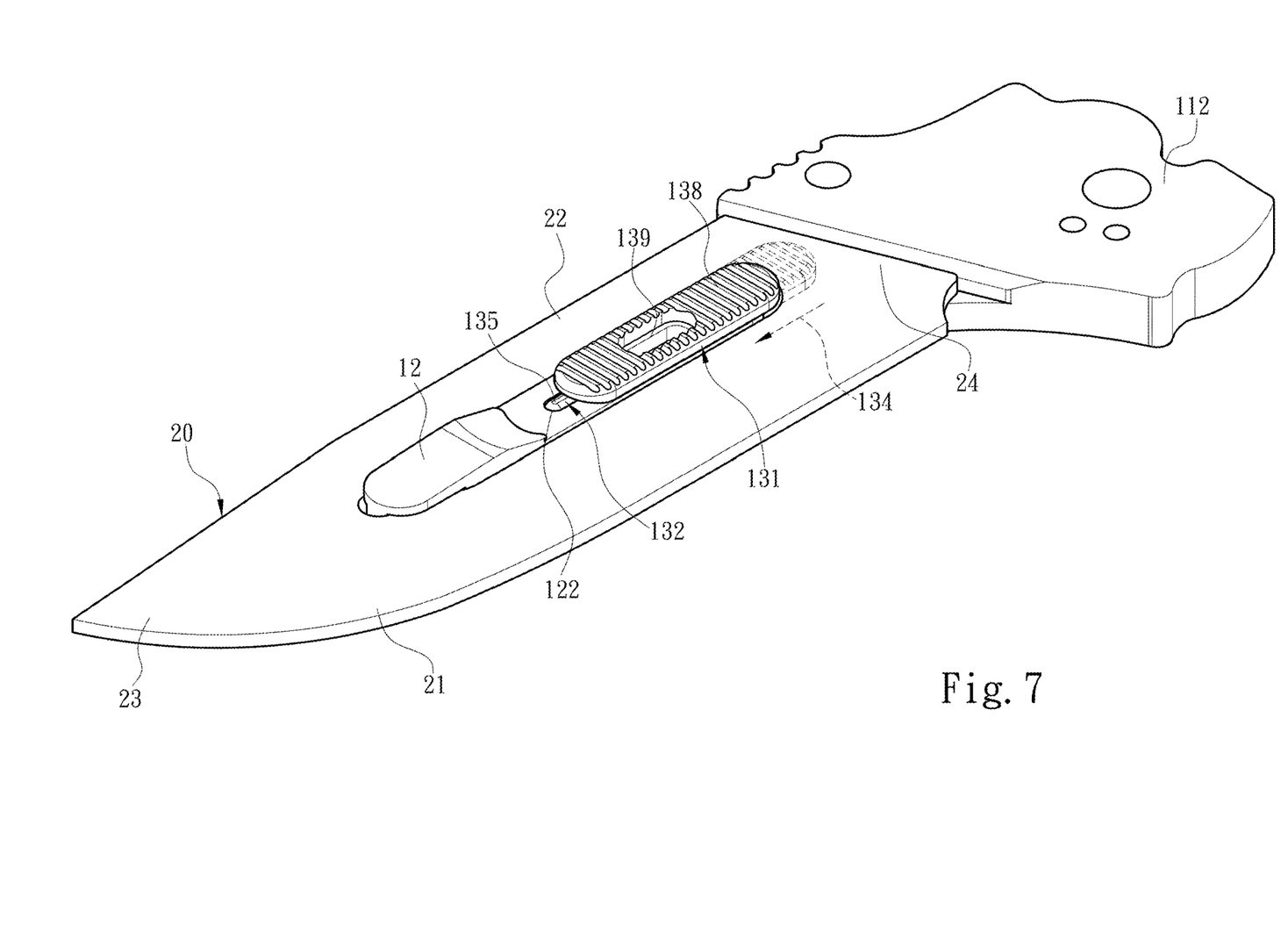
FIG. 7 is a perspective structural view of the cutting tool entering a second mode according to an embodiment of the present invention.

The blade limiting assembly 13 comprises a first mode and a second mode after the replaceable blade 20 is mounted on the blade holder 10. In the first mode, the limiting block 132 enters the stop position to prohibit the heel 24 from detaching from the blade holder 10 by the limiting member 131. In a second mode, the limiting block 132 enters the release position to allow the limiting member 131 to switch position so that the replaceable blade 20 is detached relative to the blade holder 10. The basic operation of the replaceable blade 20 and the blade holder 10 is the same as that of the prior art including U.S. Pat. No. 8,074,364B2, US 2017/0151682A1, US 2019/0217489A1, which will not be further described in the specification. The blade limiting assembly 13 is described as follow. Before the blade holder 10 is assembled with the replaceable blade 20, the blade limiting assembly 13 needs to enter the second mode, so that the replaceable blade 20 can be assembled with the blade holder 10 in a conventional manner. When the narrow hole section 223 of the long assembling hole 221 is engaged with the assembling rail 121, the limiting member 131 is pushed, so that the limiting member 131 enters the limited position. At the same time, the limiting block 132 is no longer pressed by the limiting member 131, and is moved from the release position to the stop position, so that the blade limiting assembly 13 enters the first mode. In the first mode, the limiting member 131 and the limiting block 132 interlock with each other. Unless the limiting block 132 is pressed by an external force, the limiting member 131 is in the limited position persistently. Thus, the replaceable blade 20 does not detach erroneously during the use of the blade holder 10.

Figure 4:
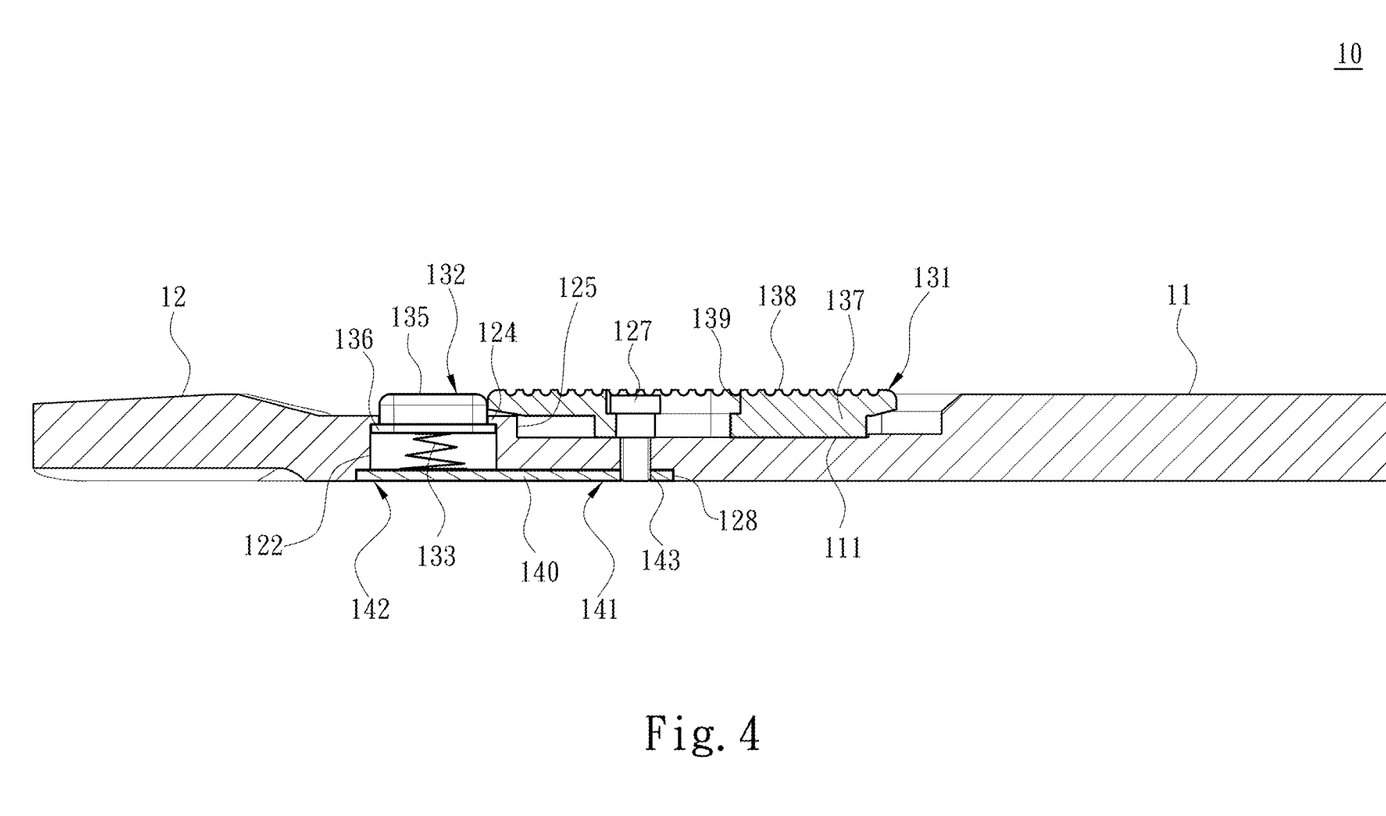
FIG. 4 is a first cross-sectional view of the blade holder according to an embodiment of the present invention.
Figure 5:
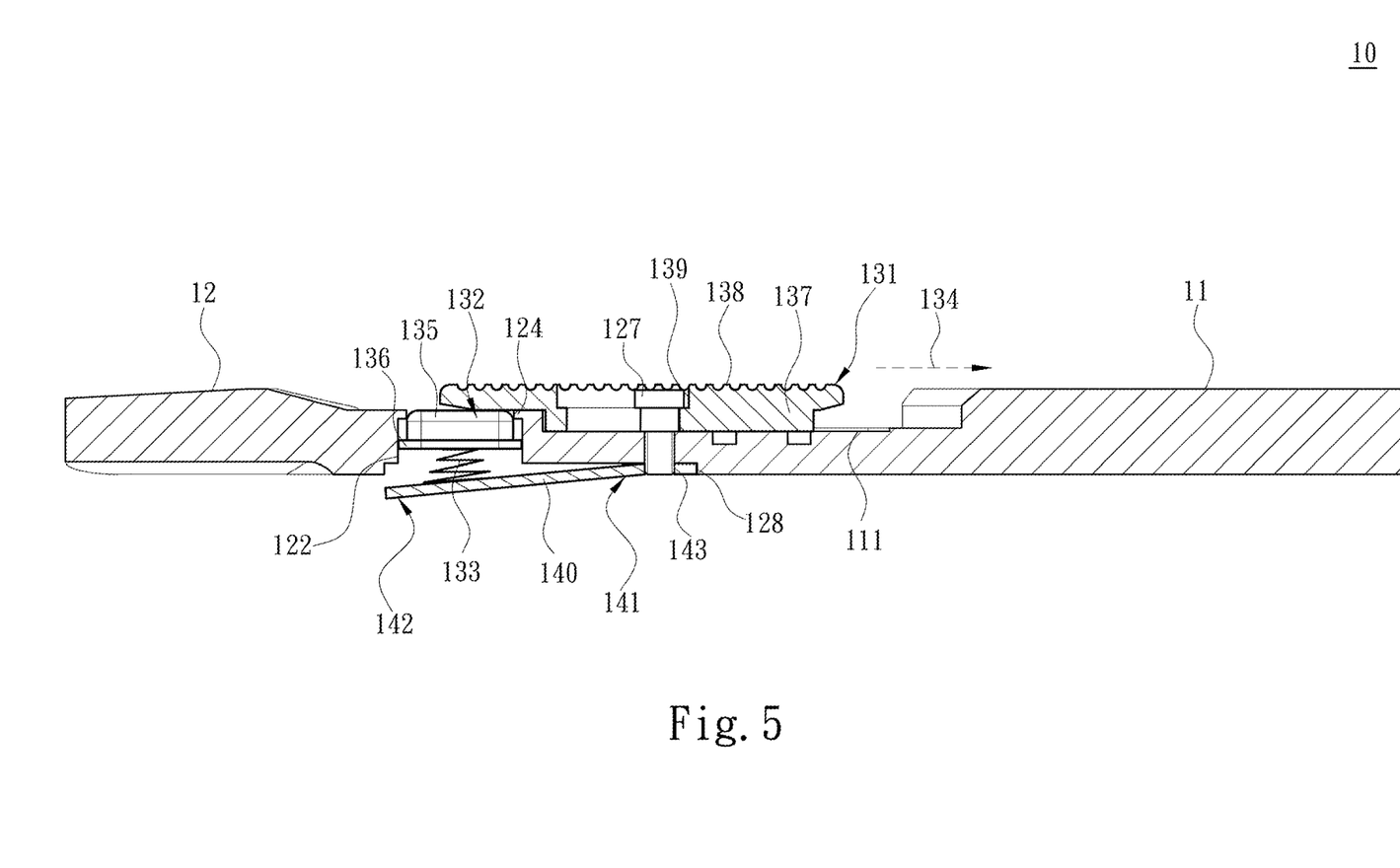
FIG. 5 is a second cross-sectional view of the blade holder according to an embodiment of the present invention.

Please refer to FIG. 4 and FIG. 5. In one embodiment, a first protruded rib 124 is provided in the first mounting hole 122 to prevent the limiting block 132 from detaching, and the limiting block 132 comprises a main body 135 and a second protruded rib 136 disposed on one edge of the main body 135 to abut against the first protruded rib 124 when the limiting block 132 enters the stop position. In this embodiment, the first mounting hole 122 penetrates the mounting rod 12 and closes an opening of the first mounting hole 122 adjacent the elastic member 133 after the limiting block 132 and the elastic member 133 are assembled and placed in the first mounting hole 122, thus the elastic member 133 is fixed on a closed structure. Furthermore, the first protruded rib 124 is located at an opening of the first mounting hole 122 adjacent the limiting block 132.

Please refer to FIG. 2, FIG. 3, FIG. 4, and FIG. 5. In one embodiment, the mounting rod 12 is provided with a mounting slot 125 on one side where the limiting block 132 protrudes, and the limiting member 131 comprises a mounting portion 137 placed in the mounting slot 125, and a push portion 138 connected to the mounting portion 137 and located on the surface of the mounting rod 12. Further, a length of the mounting portion 137 is shorter than a length of the mounting slot 125 to allow the mounting portion 137 to slide in the mounting slot 125. In one embodiment, in order to avoid a volume of the mounting rod 12 being too large due to requirement of the length of the mounting slot 125, the mounting slot 125 is opened at one side facing the supporting base 11, and the supporting base 11 comprises a groove 111 disposed extendedly from the mounting slot 125 for the mounting portion 137 to slide in the groove 111. Further, a groove bottom of the groove 111 and a groove bottom of the mounting slot 125 are located on a same plane. Accordingly, when the limiting member 131 enters the limited position, the mounting portion 137 will be partially located in the mounting slot 125 and partially located in the groove 111. Furthermore, the limiting member 131 comprises a long hole 139 penetrating the mounting portion 137 and the push portion 138, and the mounting rod 12 comprises a second mounting hole 126 opened in the mounting slot 125, and a positioning member 127 passing through the long hole 139 to be assembled in the second mounting hole 126. In addition to connecting the limiting member 131 with the mounting rod 12, the positioning member 127 is also capable of serving as a stopping point when the limiting member 131 is moved in the direction toward the supporting base 11.

Please refer to FIG. 2 FIG. 3, FIG. 4, and FIG. 5. In one embodiment, the first mounting hole 122 and the second mounting hole 126 penetrate the mounting rod 12 respectively, the blade limiting assembly 13 comprises a supporting plate 140 provided on one side of the mounting rod 12 without the limiting block 132 protruding from, and the supporting plate 140 is provided for assembling the positioning member 127 and the elastic member 133. Further, the supporting plate 140 comprises a fixed end 141 assembled with the positioning member 127, and a free end 142 assembled with the elastic member 133 and displacing in a direction opposite to the mounting rod 12 when the limiting block 132 is in the release position. In addition, a third mounting hole 143 is formed at the fixed end 141 of the supporting plate 140 for assembling the positioning member 127. In another embodiment, one side of the mounting rod 12 for assembling the supporting plate 140 predeterminately is formed with an accommodating groove 128 provided for disposing the supporting plate 140.

Please refer to FIG. 1 and FIG. 2. In one embodiment, the supporting base 11 comprises a hinge joint portion 112 assembling with the shank 30. Thereby, the blade holder 10 can form the structure of a folding blade.

What is claimed is:

1. A blade holder for assembling a replaceable blade thereon, the replaceable blade comprising a long assembling hole, the long assembling hole comprising a wide hole section and a narrow hole section communicating with the wide hole section and being close to a blade point of the replaceable blade, the blade holder comprising:

a supporting base assembled with a shank and provided for a heel of the replaceable blade to dispose thereon;

a mounting rod integrally extended from the supporting base and capable of being placed in the wide hole section, the mounting rod comprising an assembling rail disposed at one end thereof opposite to the supporting base and a first mounting hole, wherein the assembling rail is engaged with the narrow hole section when the replaceable blade is assembled in a direction toward the supporting base; and a blade limiting assembly comprising a limiting member provided on the mounting rod and controlled to move a displacement stroke relative to the mounting rod, a limiting block provided in the first mounting hole, and an elastic member provided in the first mounting hole and connected to the limiting block, the limiting member comprising a limited position and an unblocked position in the displacement stroke, the limiting block located on a path of the displacement stroke, the limiting block comprising a stop position in which the limiting block protrudes a surface of the mounting rod to force the limiting member to locate at the limited position, and a release position in which the limiting block sinks into the first mounting hole to allow the limiting member to switch between the limited position and the unblocked position, the blade limiting assembly comprising a first mode in which the limiting block enters the stop position to prohibit the heel from detaching from the blade holder by the limiting member when the replaceable blade is mounted on the blade holder, and a second mode in which the limiting block enters the release position to allow the limiting member to switch its position so that the replaceable blade is detached from the blade holder.

2. The blade holder for assembling the replaceable blade thereon as claimed in claim 1, wherein a first protruded rib is provided in the first mounting hole to prevent the limiting block from detaching, and the limiting block comprises a main body and a second protruded rib disposed on one edge of the main body to abut against the first protruded rib when the limiting block enters the stop position.

3. The blade holder for assembling the replaceable blade thereon as claimed in claim 2, wherein the mounting rod is provided with a mounting slot on one side thereof where the limiting block protrudes, and the limiting member comprises a mounting portion placed in the mounting slot, and a push portion connected to the mounting portion and located on the surface of the mounting rod.

4. The blade holder for assembling the replaceable blade thereon as claimed in claim 3, wherein the mounting slot is opened at one side thereof facing the supporting base, and the supporting base comprises a groove disposed extendedly from the mounting slot for the mounting portion to slide in the groove.

5. The blade holder for assembling the replaceable blade thereon as claimed in claim 4, wherein the limiting member comprises a long hole penetrating the mounting portion and the push portion, and the mounting rod comprises a second mounting hole opened in the mounting slot, and a positioning member passing through the long hole to be assembled in the second mounting hole.

6. The blade holder for assembling the replaceable blade thereon as claimed in claim 5, wherein the first mounting hole and the second mounting hole penetrate the mounting rod, the blade limiting assembly comprises a supporting plate provided on one side of the mounting rod without the limiting block protruding from, and the supporting plate is provided for assembling the positioning member and the elastic member.

7. The blade holder for assembling the replaceable blade thereon as claimed in claim 6, wherein the supporting plate comprises a fixed end assembled with the positioning member, and a free end assembled with the elastic member and displacing in a direction opposite to the mounting rod when the limiting block is in the release position.

8. The blade holder for assembling the replaceable blade thereon as claimed in claim 7, wherein the supporting base comprises a hinge joint portion assembling with the shank.

9. The blade holder for assembling the replaceable blade thereon as claimed in claim 1, wherein the mounting rod is provided with a mounting slot on one side thereof where the limiting block protrudes, and the limiting member comprises a mounting portion placed in the mounting slot, and a push portion connected to the mounting portion and located on the surface of the mounting rod.

10. The blade holder for assembling the replaceable blade thereon as claimed in claim 9, wherein the mounting slot is opened at one side thereof facing the supporting base, and the supporting base comprises a groove disposed extendedly from the mounting slot for the mounting portion to slide in the groove.

11. The blade holder for assembling the replaceable blade thereon as claimed in claim 10, wherein the limiting member comprises a long hole penetrating the mounting portion and the push portion, and the mounting rod comprises a second mounting hole opened in the mounting slot, and a positioning member passing through the long hole to be assembled in the second mounting hole.

12. The blade holder for assembling the replaceable blade thereon as claimed in claim 11, wherein the first mounting hole and the second mounting hole penetrate the mounting rod, the blade limiting assembly comprises a supporting plate provided on one side of the mounting rod without the limiting block protruding from, and the supporting plate is provided for assembling the positioning member and the elastic member.

13. The blade holder for assembling the replaceable blade thereon as claimed in claim 12, wherein the supporting plate comprises a fixed end assembled with the positioning member, and a free end assembled with the elastic member and displacing in a direction opposite to the mounting rod when the limiting block is in the release position.

14. The blade holder for assembling the replaceable blade thereon as claimed in claim 1, wherein the supporting base comprises a hinge joint portion assembling with the shank.

* * * * *